United States Patent [19]

Jacobson et al.

[11] Patent Number: 4,742,072

[45] Date of Patent: May 3, 1988

[54] 1-DIMETHYLCARBAMOYL-3-T-BUTYL-5-SUBSTITUTED-1H-1,2,4-TRIAZOLES

[75] Inventors: Richard M. Jacobson, Chalfont; Muthuvelu Thirugnanam, Langhorne, both of Pa.

[73] Assignee: Rohm and Haas Company, Philadelphia, Pa.

[21] Appl. No.: 759,016

[22] Filed: Jul. 25, 1985

[51] Int. Cl.$^4$ ............... C07D 249/12; A01N 43/653
[52] U.S. Cl. .................................. 514/384; 548/265
[58] Field of Search .................. 548/265; 514/384

[56] References Cited

U.S. PATENT DOCUMENTS

| | | | |
|---|---|---|---|
| 3,308,131 | 3/1967 | McKusick | 548/265 |
| 3,973,028 | 8/1976 | Doyle, Jr. et al. | 548/265 |
| 4,038,387 | 7/1977 | Doyle, Jr. et al. | 548/265 |
| 4,054,664 | 10/1977 | Watkins et al. | 548/265 |
| 4,160,839 | 7/1979 | Kirkpatrick | 548/265 |
| 4,220,790 | 9/1980 | Kirkpatrick | 548/265 |
| 4,255,435 | 3/1981 | Watkins et al. | 548/262 |
| 4,291,043 | 9/1981 | Kristiansen et al. | 548/265 |

FOREIGN PATENT DOCUMENTS 0029407  5/1981  European Pat. Off. ............ 548/265

OTHER PUBLICATIONS

Gupta, A. and Misra, H., "Synthesis and Pesticidal Activities of Some New Substituted 1,2,4-Triazoles and Their Derivatives," *Agric. Biol. Chem.*, 44, pp. 1009–1013 (1980).

McCalley, N., "Cabbage Aphid Control on Brussels Sprouts and Broccoli," *California Agriculture*, pp. 7–8 (1982).

*Primary Examiner*—Richard L. Raymond
*Assistant Examiner*—D. L. Dinner
*Attorney, Agent, or Firm*—Douglas E. Winters; John C. Demeter

[57] ABSTRACT

This invention relates to 1-dimethylcarbamoyl-3-t-butyl-5-(carboalkoxy)-alkylthio-1H-1,2,4-triazoles as defined herein, compositions containing those compounds and methods of use.

44 Claims, No Drawings

1-DIMETHYLCARBAMOYL-3-T-BUTYL-5-SUBSTITUTED-1H-1,2,4-TRIAZOLES

BACKGROUND OF THE INVENTION

This invention relates to novel 1-dimethylcarbamoyl-3-t-butyl-5-(carboalkoxy)alkylthio-1H-1,2,4-triazoles which are useful as insecticides, molluscicides and plant growth regulating agents, compositions containing those compounds and methods of use.

The search for compounds which have a combination of excellent activity and essentially no undesired toxicity is a continuing one due to recognition of the possible toxicity to animals and humans of many known pesticides.

Certain 1,2,4-triazoles have been disclosed as having pesticidal activity.

U.S. Pat. No. 3,308,131 describes a group of 1,2,4-triazoles having the general formula

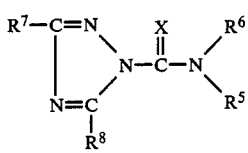

and

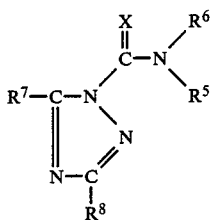

where X is oxygen or sulfur, $R^5$ and $R^6$ are aliphatic groups containing up to 14 carbons and which may be joined to form a heterocyclic ring with the carbamoyl nitrogen atom and $R^7$ and $R^8$, which together contain up to 14 carbon atoms, are free from aliphatic unsaturation and are selected from hydrogen, halogen, sulfonyl, mercapto, cyano, hydrocarbyl, halohydrocarbyl, nitrohydrocarbyl, hydroxycarbyloxycarbonylhydrocarbyl, hydrocarbylsulfonyl, hydrocarbylmercapto, nitrohydrocarbylmercapto, halohydrocarbylmercapto, aminohydrocarbylmercapto and hydrocarbyloxyhydrocarbyl. These compounds are said to be useful as insecticides, in dyeing textiles and as analgesics.

U.S. Pat. No. 4,291,043 describes 1-N,N-dimethylcarbamoyl-3(5)-alkyl-5(3)-alkylthioalkylthio-1,2,4-triazoles having insecticidal activity. The 3(5) substituents include i-propyl, s-butyl, t-butyl or optionally methyl-substituted cyclopropyl and a group having the formula

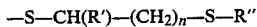

where R' is H or methyl, R'' is lower ($C_1$–$C_4$)alkyl and n is zero or 1.

U.S. Pat. No. 3,973,028 describes 1-dimethylcarbamoyl-3-branched alkyl-1,2,4-triazol-5-yl-(N-substituted)-sulfonamides having insecticidal activity.

U.S. Pat. No. 4,054,664 describes 1(2)-(N,N-disubstituted carbamoyl)-3,5-substituted-1,2,4-triazoles having insecticidal activity. The 3(5) substituents include isopropyl), s-butyl, t-butyl, and S—R where R is methyl, ethyl, propyl, vinyl, prop-2-ynyl, but-2-enyl or 2-haloalkyl.

U.S. Pat. No. 4,160,839 discloses 1-N,N-dimethylcarbamoyl-3,5-substituted-1,2,4-triazoles having insecticidal activity. The 3-substituents include t-butyl, propyl, cyclopropyl, isopropyl or 1-methylpropyl. The 5-substituents include S—R where R is 2-propynyl, allyl, 2-bromoallyl, 2-chloroallyl, 2-methylallyl, 1-methylallyl or 2,3,3-trichloroallyl.

U.S. Pat. No. 4,220,790 discloses 1-N,N-dimethylcarbamoyl-3-tert-butyl-5-methylthio-1,2,4-triazole having insecticidal activity.

The present invention discloses 1-dimethylcarbamoyl-3-t-butyl-5-(carboalkoxy)-alkylthio-1H-1,2,4-triazoles. These compounds are distinguished primarily by their novel 5-position substituents.

Compounds of the present invention are also distinguished by their excellent insecticidal activity against sucking insects such as those of the order Homoptera and especially those of the family Aphididae; that is, these compounds are highly selective. More particularly, these compounds possess very good contact action and are plant systemic through both foliar and root absorption. Further, compounds of the present invention exhibit very good residual properties through both foliar and root absorption and transport.

Certain compounds of the present invention are also distinguished by their plant growth regulator effect. Further, certain compounds of the present invention are distinguished by their molluscicidal activity.

Accordingly, compounds of the present invention are particularly suitable for controlling plant-destructive insects in crops of cultivated plants and ornamentals, especially in crops of fruits, vegetables and cereals. Certain compounds are suitable as plant growth regulating agents and certain compounds are suitable for controlling molluscs.

It is therefore an objective of the present invention to provide novel compounds, and compositions containing said compounds, which possess one or more of insecticidal, plant growth regulatory and molluscicidal activity. It is a further object of this invention to provide methods for controlling insects, regulating plant growth and/or controlling molluscs using the novel compounds.

SUMMARY OF THE INVENTION

In accordance with the present invention, there are provided compounds having the formula:

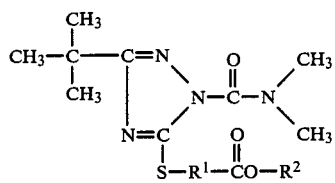

wherein
$R^1$ is an unsubstituted or substituted ($C_1$–$C_{10}$)-alkylidene ($—CH_2)_n—$) group having one to four of the same or different substituents $CO_2R$ or ($C_1$–$C_6$) alkyl
$R^2$ is hydrogen or ($C_1$–$C_6$) alkyl
where R, is hydrogen or ($C_1$–$C_6$)alkyl and agronomically acceptable salts thereof.

Further, in accordance with the present invention, there are provided compositions containing compounds of the present invention and methods of using said compounds and compositions.

DETAILED DESCRIPTION OF THE INVENTION

The term "alkyl" should be understood as including straight or branched chain groups such as methyl, ethyl, n-propyl, isopropyl, n-butyl, t-butyl, isobutyl, neopentyl and the like.

1-dimethylcarbamoyl-3-t-butyl-5-(1-(carbo-(1-carbomethoxyethoxy))-prop-2-ylthio)-1H-1,2,4-triazole
1-dimethylcarbamoyl-3-t-butyl-5-(1-(carbo-(2-carbomethoxyethoxy))-prop-2-ylthio)-1H-1,2,4-triazole
1-dimethylcarbamoyl-3-t-butyl-5-(1-(carbo-(2-carboxyethoxy))-1-propyl-eth-2-ylthio)-1H-1,2,4-triazole
1-dimethylcarbamoyl-3-t-butyl-5-(1-(carbo-(2-carboxyethoxy))-prop-2-ylthio)-1H-1,2,4-triazole
1-dimethylcarbamoyl-3-t-butyl-5-(1-(carbo-i-propoxy)-1-carbomethoxy-eth-2-ylthio)-1H-1,2,4-triazole
1-dimethylcarbamoyl-3-t-butyl-5-(1-(carbo-i-propoxy)-prop-2-ylthio)-1H-1,2,4-triazole
1-dimethylcarbamoyl-3-t-butyl-5-(1-(carbo-t-butoxy)-prop-2-ylthio)-1H-1,2,4-triazole
1-dimethylcarbamoyl-3-t-butyl-5-(1-(carboethoxy)-prop-3-ylthio)-1H-1,2,4-triazole
1-dimethylcarbamoyl-3-t-butyl-5-(1-(carbomethoxy)-prop-2-ylthio)-1H-1,2,4-triazole
1-dimethylcarbamoyl-3-t-butyl-5-(1-carbopropoxy)-prop-2-ylthio)-1H-1,2,4-triazole
1-dimethylcarbamoyl-3-t-butyl-5-(1-(carboxy)-prop-2-ylthio)-1H-1,2,4-triazole sodium salt
1-dimethylcarbamoyl-3-t-butyl-5-(carbo-(propargyloxy)methylthio)-1H-1,2,4-triazole
1-dimethylcarbamoyl-3-t-butyl-5-(carbo-i-propoxymethylthio)-1H-1,2,4-triazole
1-dimethylcarbamoyl-3-t-butyl-5-(carbo-t-butoxymethylthio)-1H-1,2,4-triazole
1-dimethylcarbamoyl-3-t-butyl-5-(carboethoxy-methylthio)-1H-1,2,4-triazole
1-dimethylcarbamoyl-3-t-butyl-5-(carbomethoxymethylthio)-1H-1,2,4-triazole
1-dimethylcarbamoyl-3-t-butyl-5-(carbopropoxymethylthio)-1H-1,2,4-triazole
1-dimethylcarbamoyl-3-t-butyl-5-(carboxy-methylthio)-1H-1,2,4-triazole
1-dimethylcarbamoyl-3-t-butyl-5-(carboxy-methylthio)-1H-1,2,4-triazole sodium salt
1-dimethylcarbamoyl-3-t-butyl-5-carbomethoxymethylthio-1H-1,2,4-triazole
1-dimethylcarbamoyl-3-t-butyl-5-carboethoxymethylthio-1H-1,2,4-triazole
1-dimethylcarbamoyl-3-t-butyl-5-carbo-t-butoxymethylthio-1H-1,2,4-triazole
1-dimethylcarbamoyl-3-t-butyl-5-(1-carbomethoxyeth-1-yl)thio-1H-1,2,4-triazole
1-dimethylcarbamoyl-3-t-butyl-5-(1-carboethoxyeth-1-yl)thio-1H-1,2,4-triazole
1-dimethylcarbamoyl-3-t-butyl-5-carboxymethylthio-1H-1,2,4-triazole
1-dimethylcarbamoyl-3-t-butyl-5-carboxymethylthio-1H-1,2,4-triazole sodium salt
1-dimethylcarbamoyl-3-t-butyl-5-(2-carbomethoxyeth-1-yl)thio-1H-1,2,4-triazole
1-dimethylcarbamoyl-3-t-butyl-5-(3-carbomethoxyprop-1-yl)thio-1H-1,2,4-triazole Because of their activity, preferred compounds of the present invention are those of Formula I where $R^1$ is unsubstituted or substituted ($C_1$–$C_6$)alkylidene group having one to four substituents selected from $CO_2R$, or ($C_1$–$C_6$)alkyl, and R, is hydrogen or ($C_1$–$C_6$)alkyl.

Compounds of Formula I most preferred as homopteracides are those where $R^1$ is —$CH_2$—, —$CH_2CH_2$—, —$CH_2$—$CH_2CH_2$—, or —$CH(CH_3)$—; and $R^2$ is hydrogen or lower ($C_1$–$C_4$)alkyl.

Compounds of Formula I most preferred as plant growth regulators are those where $R^1$ is —$CH_2$—;

X is —$CO_2$—; and $R^2$ is hydrogen, methyl or ethyl.

Compounds of Formula I most preferred as molluscicides are those where $R^1$ is —$CH_2$—;

X is —$CO_2$—; and $R^2$ is ethyl.

Since the 1-dimethylcarbamoyl-3-t-butyl-5-(carboalkoxy)-alkylthio-1H-1,2,4-triazoles of Formula I may possess acidic or basic functional groups, they may form novel salts with appropriate bases or acids which also exhibit insecticidal activity. Typical salts are the agronomically acceptable metal salts, ammonium salts and acid addition salts. Among the metal salts are those in which the metal cation is an alkali metal cation such as sodium, potassium, lithium or the like; alkaline earth metal cation such as calcium, magnesium, barium, strontium or the like; or heavy metal cation such as zinc, manganese, cupric, cuprous, ferric, ferrous, titanium, aluminum or the like. Among the ammonium salts are those in which the ammonium cation has the formula $NR^9R^{10}R^{11}R^{12}$ wherein each of $R^9$, $R^{10}$, $R^{11}$ and $R^{12}$ are independently a hydrogen atom, a hydroxy group, a ($C_1$–$C_4$)alkoxy group, a ($C_1$–$C_{20}$)alkyl group, a ($C_3$–$C_8$)alkenyl group, a ($C_3$–$C_8$)alkynyl group, a ($C_2$–$C_8$)hydroxyalkyl group, a ($C_2$–$C_8$)alkoxyalkyl group, a ($C_2$–$C_6$)aminoalkyl group, a ($C_2$–$C_6$)haloalkyl group, an amino group, a ($C_1$–$C_4$)alkyl or ($C_1$–$C_4$)dialkylamino group, a substituted or unsubstituted phenyl group, a substituted or unsubstituted phenylalkyl group, having up to four carbon atoms in the alkyl moiety, or any two of $R^9$, $R^{10}$, $R^{11}$ or $R^{12}$ can be taken together to form with the nitrogen atom a 5- or 6-membered heterocyclic ring, optionally having up to one additional hetero atom (e.g., oxygen, nitrogen, or sulfur) in the ring, and preferably saturated, such as piperidino, morpholino, pyrrolidino, piperazino or the like, or any three of $R^9$, $R^{10}$, $R^{11}$ or $R^{12}$ can be taken together to form with the nitrogen atom a 5- or 6-membered aromatic heterocyclic ring, such as piperazole or pyridine. When the ammonium group contains a substituted phenyl or substituted phenylalkyl group, the substituents will generally be selected from halogen atoms, ($C_1$–$C_8$)alkyl groups, ($C_1$–$C_4$)alkoxy groups, hydroxy group, nitro groups, trifluoromethyl groups, cyano groups, amino groups, ($C_1$–$C_4$)alkylthio groups, and the like. Such substituted phenyl groups preferably have up to two such substituents. Representative ammonium cations include ammonium, dimethylammonium, 2-ethylhexylammonium, bis(2-hydroxyethyl)ammonium, tris(2-hydroxyethyl)ammonium, dicyclohexylammonium, t-octylammonium, 2-hydroxyethylammonium, morpholinium, piperidinium, 2-phenethylammonium, 2-methylbenzylammonium, n-hexylammonium, triethylammonium, trimethylammonium, tri(n-butyl)-ammonium, methoxyethylammonium, diisopropylammonium, pyridinium, dialkylammonium, pyrazolium, propargylammonium, dimethylhydrazinium, octadecylammonium, 4-dichlorophenylammonium, 4-nitrobenzylammonium, benzyltrimethylammonium, 2-hydroxyethyldimethyloctadecylammonium, 2-hydroxyethyldiethyloctylammonium, decyltrimethylammonium, hexyltriethylammonium, 4-methylbenzyltrimethylammonium, and the like. Among the acid addition salts are those in which the anion is an agronomically acceptable anion such as chloride, bromide, sulfate, nitrate, perchlorate, acetate, oxalate and the like.

The 1-dimethylcarbamoyl-3-t-butyl-5-(carboalkoxy)-alkylthio-1H-1,2,4-triazoles of the present invention or their precursors are prepared by S-alkylating a 3-t-butyl-5-thio-1H-1,2,4-triazole in the presence of a solvent or diluent which is inert to the reactants and optionally an acid scavenger with a compound having the formula

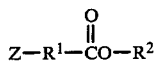
            II where $R^1$ and $R^2$ are as defined above for Formula I and Z is a good leaving group such as halo (chloro, bromo or iodo), alkyl sulfonates such as methane sulfonate, or phenyl or substituted phenyl sulfonates such as paratoluene sulfonate to obtain 3-t-butyl-5-(carboalkoxy)alkylthio-1H-1,2,4-triazoles.

Suitable solvents or diluents for the above process include methanol, ethanol, tetrahydrofuran, dimethylformamide, or acetonitrile.

Suitable acid scavengers for the above process, such as diisopropylethylamine may be added during alkylation or, if desired, the 3-t-butyl-5-thio-1H-1,2,4-triazole could be pretreated with an acid scavenger such as sodium hydride, sodium hydroxide, potassium hydroxide or the like.

Modifications to the above process may be necessary to accommodate reactive functionalities of particular 5-substituents. Such modifications would be apparent and known to those skilled in the art.

The 3-t-butyl-5-(carboalkoxy)alkylthio-1H-1,2,4-triazole obtained by the above process is then reacted with a compound having the formula

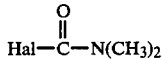
            III where Hal is halogen (chloro, bromo or iodo) in the presence of a suitable acid scavenger and optionally a suitable acylation catalyst.

Suitable acid scavengers for this process include tertiary amines such as triethylamine and pyridine.

Suitable acylation catalysts include 4-dimethylaminopyridine.

The compounds of Formula II can be prepared from known precursors by known methods.

The 3-t-butyl-5-thio-1H-1,2,4-triazoles used as a starting material can be prepared from known precursors by known methods as illustrated below for Example No. 2, part (a).

The agronomically acceptable salts embraced by Formula I of the invention can be prepared by reacting a metal hydroxide, a metal hydride or an amine or ammonium salt, such as a halide, hydroxide or alkoxide with a compound of Formula I having one or more carboxy groups or reacting a quaternary ammonium salt, such as chloride, bromide, nitrate or the like with a metal salt of a compound of Formula I in a suitable solvent. When metal hydroxides are used as reagents, useful solvents include water; ethers such as glyme, dioxane, tetrahydrofuran and the like; alcohols such as methanol, ethanol, isopropanol and the like. When metal hydrides are used as reagents, useful solvents include nonhydroxylic solvents, for example, ethers such as dioxane, glyme, tetrahydrofuran, diethyl ether and the like; hydrocarbons such as toluene, xylene, hexane, pentane, heptane, octane, and the like; dimethylformamide, and the like. When amines are used as reagents, useful solvents include alcohols, such as methanol or ethanol; hydrocarbons, such as toluene, xylene, hexane and the like; tetrahydrofuran; glyme; dioxane; or water. When ammonium salts are used as reagents, useful solvents include water; alcohols, such as methanol or ethanol; glyme; tetrahydrofuran; or the like. When the ammonium salt is other than a hydroxide or alkoxide, an additional base, such as potassium or sodium hydroxide, hydride, or alkoxide is generally used. The particular choice of solvent will depend on the relative solubilities of the starting materials and the resultant salts, and slurries rather than solutions of certain reagents may be used to obtain the salts. Generally, equivalent amounts of the starting reagents are used and the salt-forming reaction is carried out between about 0° C. to about 100° C., preferably at about room temperature.

The acid addition salts of the present invention can be prepared by reacting hydrochloric, hydrobromic, sulfuric, nitric, phosphoric, acetic, propionic, benzoic or other suitable acid with a compound of the present invention having a basic functional group in a suitable solvent such as water, alcohols, ethers, esters, ketones, haloalkanes and the like. The particular choice of solvent will depend on the relative solubilities of the starting materials and the resulting salts and slurries rather than solutions of certain reagents may be used to obtain the salts. Generally, equivalent molar amounts of starting materials are used and the salt-forming reaction is carried out between about −10° C. to about 100° C., preferably at about room temperature.

The following examples will further illustrate this invention but are not intended to limit it in any way. In Table I, 1-dimethylcarbamoyl-3-t-butyl-5-(carboalkoxy)-alkylthio-1H-1,2,4-triazoles of the present invention that have been made are listed. Structures were confirmed by NMR and in some cases by IR and/or elemental analysis. Specific illustrative preparation of the compounds of Examples 2, 4, 6, 7 and 10 are described after Table I.

TABLE I

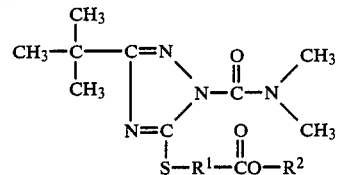

| Example No. | $R^1$ | $R^2$ |
|---|---|---|
| 1 | —CH₂— | CH₃ |
| 2 | —CH₂— | —CH₂CH₃ |
| 3 | —CH₂— | —C(CH₃)₃ |
| 4 | —CH(CH₃)— | —CH₂CH₃ |
| 5 | —CH(CH₃)— | CH₃ |
| 6 | —CH₂CH₂CH₂— | —CH₂CH₃ |

TABLE I-continued

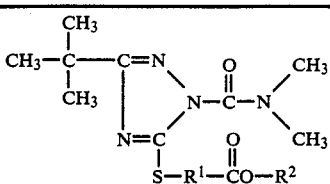

| Example No. | R¹ | R² |
|---|---|---|
| 7 | —CH₂CH₂— | CH₃ |
| 8 | —CH₂— | —CH₂CH₂CH₃ |
| 9 | —CH₂— | —CH(CH₃)₂ |
| 10 | —CH₂— | H |
| 11 | —CH₂CH₂— | —CH₂CH₃ |
| 12 | —CH₂— | Na |
| 13 | —C(CH₃)₂— | —CH₂CH₃ |
| 14 | —CH(CO₂CH₂CH₃)CH₂— | —CH₂CH₃ |
| 15 | —CH(CH₃)— | H |
| 16 | —CH₂CH₂— | H |

EXAMPLE NO. 2

Preparation of 1-dimethylcarbamoyl-3-t-butyl-5-carboethoxymethylthio-1H-1,2,4-triazole (a) Preparation of 3-t-butyl-5-thio-1H-1,2,4-triazole Into a 5 liter 4 necked flask equipped with a mechanical stirrer, reflux condenser, thermometer, and addition funnel was added 500 g (5.5 mole) of thiosemicarbazide, 1000 ml of 1,4-dioxane, and a solution of 220 g (5.5 mole) of sodium hydroxide in 920 ml of water. The mixture was stirred and cooled with an external bath to maintain the temperature at near 25° C. while 630 ml (5.1 mole) of trimethylacetyl chloride was added over the course of 30 minutes. After stirring an additional 30 minutes, the precipitated trimethylacetylthiosemicarbazide was collected by filtration and used as in the next reaction.

All of the wet trimethylacetylthiosemicarbazide was suspended in a solution of 450 g (11.25 mole) of sodium hydroxide in 1900 ml of water and the suspension was heated to 90° C. until all was in solution and then the reaction mixture was heated an additional 1 hour. After cooling the mixture was acidified with concentrated hydrochloric acid and let stand overnight. The resulting crystals were collected by filtration and washed with water and ethyl ether to yield 320 g (2.1 mole) of 3-t-butyl-5-thio-1H-1,2,4-triazole. m.p. 205° C.

(b) Preparation of 3-t-butyl-5-carboethoxymethylthio-1H-1,2,4-triazole

To 157 g (1.0 mole) of 3-t-butyl-5-thio-1H-1,2,4-triazole in 500 ml of ethanol was added 110 ml (0.99 mole) of ethyl bromoacetate. The resulting mixture was refluxed for two hours, cooled, concentrated under vacuum, and partitioned between ether and aqueous ammonium hydroxide. The organic layer was washed with brine, dried over magnesium sulfate, and concentrated under vacuum yielding 143 g (0.59 mole) 3-t-butyl-5-carboethoxymethylthio-1H-1,2,4-triazole. m.p. 93° C.

(c) Preparation of 1-dimethylcarbamoyl-3-t-butyl-5-carboethoxymethylthio-1H-1,2,4-triazole To 100 g (0.411 mole) of 3-t-butyl-5-carboethoxymethylthio-1H-1,2,4-triazole, 6 g (0.05 mole) of 4-dimethylaminopyridine, and 200 ml of pyridine was added 54 g (0.50 mole) of dimethylcarbamoyl chloride. The resulting solution was refluxed for eight hours and allowed to cool overnight. The reaction mixture was concentrated under vacuum, partitioned between ether and dilute hydrochloric acid. The organic layer was washed with water, brine, dried over magnesium sulfate, and concentrated under vacuum. Distillation yielded a fraction boiling at 148°-160° C. at 0.1 torr 100 g (0.35 mole) of 1-dimethylcarbamoyl-3-t-butyl-5-carboethoxymethylthio-1,2,4-triazole. m.p. 55° C.

EXAMPLE NO. 4

Preparation of 1-dimethylcarbamoyl-3-t-butyl-5-(1-carboethoxyethyl-thio)-1H-1,2,4-triazole By substituting Ethyl 2-bromopropionate for Ethyl bromoacetate in Example 2, step (b) and by following substantially the same procedures described for Example 2, there is obtained 1-dimethylcarbamoyl-3-t-butyl-5-(1-carboethoxyethyl-thio)-1H-1,2,4-triazole as an oil.

EXAMPLE NO. 6

Preparation of 1-dimethylcarbamoyl-3-t-butyl-5-(3-carboethoxypropylthio)-1H-1,2,4-triazole By substituting Ethyl 4-bromobutyrate for Ethyl bromoacetate in Example 2, step (b) and by following substantially the same procedure described for Example 2, there is obtained 1-dimethylcarbamoyl-3-t-butyl-5-(3-carboethoxypropylthio)-1H-1,2,4-triazole as an oil.

EXAMPLE NO. 7

Preparation of 1-dimethylcarbamoyl-3-t-butyl-5-(2-carbomethoxyethylthio)-1H-1,2,4-triazole By substituting methyl 3-bromopropionate for Ethyl bromoacetate in Example 2, step (b) and by following substantially the same procedures described for Example 2, there is obtained 1-dimethylcarbomoyl-3-t-butyl-5-(2-carbomethoxyethylthio)-1H-1,2,4-triazole as an oil.

EXAMPLE NO. 10

Preparation of 1-dimethylcarbamoyl-3-t-butyl-5-carboxymethylthio-1H-1,2,4-triazole To 1.2 g of 1-dimethylcarbamoyl-3-t-butyl-5-carboethoxymethylthio-1H-1,2,4-triazole (the compound of Example 2) in 20 ml of THF was added 4 ml of 12M HCl. After stirring for 48 h at 20° C. the reaction mixture was partitioned between ether and water, the ether layer was extracted with dilute NaOH and the resulting aqueous layer was acidified and extracted with fresh ether. The resulting ether layer was dried over magnesium sulfate, filtered and evaporated under vacuum to yield 1-dimethylcarbamoyl-3-t-butyl-5-carboxymethylthio-1H-1,2,4-triazole as an oil.

Other compounds of Formula I may be prepared by following substantially the procedures described above.

Suprisingly, many of the compounds of the present invention exhibit better insecticidal activity than the closest known compounds. Furthermore, the selectivity of these compounds, especially towards aphids, allows for plant protection without substantial adverse consequences toward beneficial insects making these compounds especially useful in integrated pest management programs. Accordingly, compounds of the present invention represent a genuine enrichment of the art.

Certain of the 1-dimethylcarbamoyl-3-t-butyl-5-(carboalkoxy)alkylthio-1H-1,2,4-triazoles of the present invention show, for example, activity at a concentration of from about 0.25 ppm to about 10 ppm against green peach aphids.

On the basis of their strong initial insecticidal activity and excellent residual insecticidal activity, compounds according to the invention may be used in low dosages in controlling pests. The amount of dosage depends on a variety of factors, for example, the substance used, the kind of pest, the formulation used, the state of the crop infected with the pest and the prevailing weather conditions. In general, for the control of pests in agriculture and horticulture, a dosage corresponding to from about 10 grams to about 5000 grams of the active substance per hectare may be used and from about 50 grams to about 2500 grams per hectare of the active substance is preferred.

As previously noted, the compounds of the present invention are highly selective against sucking insects of the order Homoptera and especially those of the family Aphididae.

The compounds of the present invention, for practical applications, can be utilized in the form of compositions or formulations. In these compositions and formulations, the active subtance is mixed with conventional inert (i.e., plant compatible and/or pesticidally inert) diluents or extenders such as solid carrier material or liquid carrier material, of the type usable in conventional compositions or formulations. If desired, adjuvants such as surfactants, stabilizers, antifoam agents and antidraft agents may also be combined.

Examples of compositions and formulations according to the invention are aqueous solutions and dispersions, oily solutions and oil dispersions, pastes, dusting powders, wettable powders, emulsifiable concentrates, flowables, granules, baits, invert emulsions, aerosol compositions and fumigating candles.

Wettable powders, pastes, flowables and emulsifiable concentrates are concentrated preparations which are diluted with water before or during use.

Baits are preparations generally comprising a food or other substance attractive to the target pest, that includes at least one lethal or non-lethal toxicant. Lethal toxicants kill the pest upon ingesting the bait while non-lethal toxicants change the behavior and physiology of the pest for the purpose of control.

The invert emulsions are mainly used for air application, where large areas are treated with a comparatively small amount of preparation. The invert emulsion may be prepared in the spraying apparatus shortly before, or even during, the spraying operation by emulsifying water in an oil solution or an oil dispersion of the active substance.

Compositions and formulations are prepared in a known manner, for instance by extending the active compounds with conventional dispersible liquid diluent carriers and/or dispersible solid carriers optionally with the use of carrier vehicle assistants, e.g., conventional surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as halogenated hydrocarbons, e.g., dichlorodifluoromethane and trifluorochloromethane, as well as butane, propane, nitrogen and carbon dioxide; inert dispersible liquid diluent carriers, including inert organic solvents, such as aromatic hydrocarbons (e.g., benzene, toluene, xylene, alkyl naphthalenes, etc.), halogenated, especially chlorinated, aromatic hydrocarbons (e.g., chlorobenzenes, etc.), cycloalkanes, (e.g., cyclohexane, etc.), paraffins (e.g., petroleum or mineral oil fractions), chlorinated aliphatic hydrocarbons (e.g., methylene chloride, chloroethylenes, etc.), vegetable oils (e.g., soybean oil, cotton seed oil, corn oil, etc.), alcohols (e.g., methanol, ethanol, propanol, butanol, glycol, etc.) as well as ethers and esters thereof (e.g., glycol monomethyl ether, etc.), amines (e.g., ethanolamine, etc.), amides (e.g., dimethyl formamide, etc.), sulfoxides (e.g., dimethyl sulfoxide, etc.), acetonitrile, ketones (e.g., acetone, methyl ethyl ketone, methyl isobutyl ketone, cyclohexanone, etc.), and/or water; solid carriers including ground natural minerals, such as kaolins, clays, talc, chalk, quartz, attapulgite, montmorillonite or diatomaceous earth, and ground synthetic minerals, such as highly-dispersed silicic acid, alumina and silicates; solid carriers for granules include crushed and fractionated natural rocks such as calcite, marble, pumice, sepiolite and dolomite, as well as synthetic granules or inorganic and organic meals, and granules of organic material such as sawdust, coconut shells, corn cobs and tobacco stalks. The following may be chiefly considered for use as conventional carrier vehicle assistants: emulsifying agents, such as cationic and/or non-ionic and/or anionic emulsifying agents (e.g., polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Adhesives such as carboxymethylcellulose and natural and synthetic polymers in the form of powders, granules or latices, such as gum arabic, polyvinyl alcohol and polyvinyl acetate, can be used in the formulations.

If desired, it is possible to use colorants in compositions and formulations containing compounds of the present invention such as inorganic pigments, for example, iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The active compounds of the present invention may be employed alone or in the form of mixtures with one another and/or with such solid and/or liquid dispersible carrier vehicles and/or with other known compatible active agents, especially plant protection agents, such as other arthropodicides, nematicides, fungicides, bactericides, rodenticides, herbicides, fertilizers, growth-regulating agents, synergists, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1% and 99% by weight, and preferably between about 1% and 75% by weight, of the mixture. Carrier composition mixtures suitable for direct application or field application generally contemplate those in which the active compound is present in an amount substantially between about 0.0001% and 5%, preferably between about 0.001% and 3%, by weight of the mixture. Thus the present invention contemplates overall compositions which comprise mixtures of a conventional dispersible carrier such as (1) a dispersible inert finely divided carrier solid, and/or (2) a dispersible carrier liquid such as an inert organic solvent and/or water, preferably including a surface-active effective amount of a carrier vehicle assistant, (e.g., a surface-active agent, such as an emulsifying agent and/or a dispersing agent), and an amount of the active compound which is effective for the purpose in question.

The active compounds can be applied as sprays by methods commonly employed, such as conventional high-gallonage hydraulic sprays, low gallonage sprays, ultra-low-volume sprays, airblast spray, aerial sprays, and dusts. If low volume applications are desired, a solution of the compound is usually used. In ultra-low-volume applications, a liquid composition containing the active compound is usually applied as a spray (e.g., mist) by means of atomizing equipment in finely divided form (average particle size of from about 50 to about 100 microns or less) using airplane crop spraying techniques. Typically only a few liters per hectare are needed and often amounts up to about 15 to 1000 g/hectare, preferably about 40 to 600 g/hectare are sufficient. With ultra-low-volume, it is possible to use highly concentrated liquid compositions with said liquid carrier vehicles containing from about 20 to about 95% by weight of the active compound.

Furthermore, the present invention contemplates methods of selectively killing, combating or controlling pests, which comprise applying to at least one of (a) such pests and (b) the corresponding habitat thereof (i.e., the locus to be protected, for example, to a growing crop or to an area where a crop is to be grown) a correspondingly combative or toxic amount (i.e., a pesticidally effective amount) of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dry dressing, moist dressing, wet dressing, slurry dressing, encrusting and the like.

It will be realized, of course, that the concentration of the particular active compound utilized in admixture with the carrier vehicle will depend upon such factors as the type of equipment employed, method of application, area to be treated, types of pests to be controlled and degree of infestation. Therefore, in special cases it is possible to go above or below the aforementioned concentration ranges.

Granular preparations are produced for example, by taking up the active substance in a solvent and by using the resulting solution, as the case may be in the presence of a binder, to impregnate a granular carrier material, such as porous granules (for example pumice and attaclay), or chopped tobacco stems or the like.

A granular preparation (frequently termed a "pellet") may alternatively be produced by compressing the active substance together with powdered minerals in the presence of lubricants and binders and by disintegrating and straining the composite to the desired grain size.

Dusts are obtainable by intimately mixing the active substance with an inert solid carrier material in a concentration of from about 1 to about 50% by weight. Examples of suitable solid carrier materials are talc, kaolin, pipe clay, diatomaceous earth, dolomite, gypsum, chalk, bentonite, attapulgite and colloidal $SiO_2$ or mixtures of these and simular substances. Alternatively organic carrier materials such, for example, as ground walnut shells may be used.

Wettable powders and flowables are produced by mixing from about 10 to about 99 parts by weight of a solid inert carrier such, for example, as the aforementioned carrier materials with from about 1 to about 80 parts by weight of the active substance, from about 1 to about 5 parts by weight of a dispersing agent such, for example, as the lignosulfonates or alkylnaphthalene sulfonates known for this purpose and preferably also from about 0.5 to about 5 parts by weight of a wetting agent, such as fatty alcohol sulfates, or alkylarylsulfonates of fatty acid condensation products.

To produce emulsifiable concentrates the active compound is dissolved or finely divided in a suitable solvent which preferably is poorly miscible with water, an emulsifier being added to the resulting solution. Examples of suitable solvents are xylene, toluene, high-boiling aromatic petroleum distillates, for example solvent naphtha, distilled tar oil and mixtures of these liquids. Examples of suitable emulsifiers are alkylphenoxypolyglycol ethers, polyoxyethylene sorbitan esters of fatty acids or polyoxyethylene sorbitol esters of fatty acids. The concentration of the active compound in these emulsifiable concentrates is not restricted within narrow limits and may vary between about 2% and about 50% by weight. A suitable liquid highly concentrated primary composition other than an emulsifiable concentrate is a solution of the active substance in a liquid which is readily miscible with water, for example, acetone, to which solution a dispersent and, as the case may be, a wetting agent are added. When such a primary composition is diluted with water shortly before or during the spraying operation an aqueous dispersion of the active substance is obtained.

An aerosol preparation according to the invention is obtained in the usual manner by incorporating the active substance or a solution thereof in a suitable solvent in a volatile liquid suitable for use as a propellant such, for example, as a mixture of chlorine and fluorine derivatives of methane and ethane.

Fumigating candles or fumigating powders, i.e. preparations which when burning are capable of emitting a pesticidal smoke, are obtained by taking up the active substance in a combustible mixture which may, for example, comprise a sugar or a wood, preferably in the ground form, as a fuel, a substance to sustain combustion such, for example, as ammonium nitrate or potassium chlorate, and furthermore a substance for retarding combustion, for example kaolin, bentonite and/or colloidal silicic acid.

A bait preparation comprises a food or other substance attractive to pests, a carrier, the toxicant and may optionally include other substances commonly used in preparations of this kind, such as, a preservative to inhibit bacterial and fungal growth, a waterproofing agent to prevent disintegration under wet conditions and dyes or colorants as described above.

In addition to the aforementioned ingredients the preparations according to the invention may also contain other substances commonly used in preparations of this kind.

For example, a lubricant, such as calcium stearate or magnesium stearate, may be added to a wettable powder or to a mixture to be granulated. Furthermore there may, for example, be added "adhesives" such as polyvinylalcoholcellulose derivatives or other colloidal materials, such as casein, to improve the adherence of the pesticide to the surface to be protected.

Representative preparation of compositions and formulations including the compounds of the present invention are set forth below as Examples A through I by way of illustration but not limitation. It should be understood that when compositions and formulations are prepared for use as a plant growth regulator, "toxicant" refers to an active ingredient compound of Formula I.

EXAMPLE A

Granular

| Ingredient | %/wt. |
| --- | --- |
| Toxicant | 0.25 |
| Triton ® X-305 (binder) | 0.25 |
| Agsorb ® 24/48 (diluent) | 99.50 |

Preparation: The toxicant and Triton ® X-305 are dissolved into methylene chloride and the mixture is added to the Agsorb ® with continuous mixing. The methylene chloride is then allowed to evaporate.

EXAMPLE B

Dust

| Ingredient | %/wt. |
| --- | --- |
| Toxicant | 1.0 |
| Talc | 99.0 |

Preparation: Toxicant is dissolved in excess acetone and the mixture is impregnated onto the talc. The acetone is then permitted to evaporate.

EXAMPLE C

Wettable Powder

| Ingredient | %/wt. |
| --- | --- |
| Toxicant | 25.0 |
| Toxicant impurities | 6.3 |
| Duponal ® WA Dry (wetter) | 2.0 |
| Reax ® 45A (dispersant) | 5.0 |
| Barden clay (diluent) | 31.7 |
| HiSil ® 233 (diluent) | 30.0 |

Preparation: The toxicant is absorbed onto the Barden clay and HiSil ® carriers. The Duponal ® and Reax ® are then added and the entire dry mixture blended until homogeneous. The composition is then micronized to a fine particle size.

EXAMPLE D

Emulsifiable Concentrate

| Ingredient | %/wt. |
| --- | --- |
| Toxicant | 13.5 |
| Toxicant impurities | 1.5 |
| Sponto ® 232T (emulsifier) | 6.0 |
| Sponto ® 234T (emulsifier) | 4.0 |
| Cyclohexanone (solvent) | 22.5 |
| Tenneco ® 500-100 (solvent) | 52.5 |

Preparation: All ingredients are mixed together with continuous agitation until a homogeneous clear solution is obtained.

EXAMPLE E

Aerosol

| Ingredient | %/wt. |
| --- | --- |
| Toxicant | 0.5 |
| Freon 12 | 99.5 |

Preparation: The components are mixed and packaged under pressure in a suitable container equipped with a release spray valve.

EXAMPLE F

Fumigating Candle or Fumigating Powder

| Ingredient | %/wt. |
| --- | --- |
| Toxicant | 1.0 |
| Wood dust | 96.0 |
| Starch | 3.0 |

Preparation: Toxicant, wood dust, and starch are blended together and then molded into a candle using a small amount of water to activate the starch.

EXAMPLE G

Bait

Method A

| Ingredient | %/wt. |
| --- | --- |
| Toxicant | 1.00 |
| Wheat Bran (carrier and attractant) | 89.95 |
| Corn Syrup (attractant) | 7.00 |
| Corn Oil (attractant) | 2.00 |
| Kathon ® 4200 (preservative) | 0.05 |

Preparation: The corn oil and corn syrup are added to the wheat bran with adequate mixing. The toxicant and Kathon ® are premixed with excess acetone and this solution is added to the wheat bran base with continued mixing. The acetone is then permitted to evaporate.

Method B

| Ingredient | %/wt. |
| --- | --- |
| Toxicant | 0.06 |
| Granulated Sugar (carrier and attractant) | 99.94 |

EXAMPLE H

Pellet

Same as Example G, Method A, with this addition: the bait composition is formed into ¼" diameter by ⅜" long pellets using a suitable die and press apparatus.

EXAMPLE I

Flowable

| Ingredient | %/wt. |
| --- | --- |
| Toxicant | 25.0 |
| Toxicant impurities | 6.3 |
| Duponal ® WA Dry (wetter) | 2.0 |
| Reax ® 45A (dispersant) | 5.0 |
| HiSil ® 233 (diluent) | 30.0 |
| Kelzan ® (thickener) | 0.5 |
| Water | 31.2 |

Preparation: The toxicant is absorbed onto the HiSil ® carrier. The Duponal ® and Reax ® are then added and the entire dry mixture blended until homogeneous. The composition is then micronized to a fine particle size. The resulting powder is suspended in water and the Kelzan ® added.

Compositions and formulations according to the present invention may also include known pesticidal compounds. This expands the spectrum of activity of the preparations and may give rise to synergism.

The following known insecticidal, fungicidal and acaricidal compounds are suitable for use in such a combined preparation. Insecticides such as:

Chlorinated hydrocarbons, for example, 2,2-bis(p-chlorophenyl)-1,1,1-trichloroethane and hexachloro-epoxyoctahydrodimethanonaphthalene;

Carbamates, for example N-methyl-1-naphthylcarbamate;

Dinitrophenols, for example 2-methyl-4,6-dinitrophenol and (2-(2-butyl)-4,6-dinitrophenol-3,3-dimethylacrylate;

Organic phosphorus compounds, such as dimethyl-2-methoxycarbonyl-1-methylvinyl phosphate, O,O-diethyl-O-p-nitrophenylphosphorus thioate; N-monomethylamide of O,O-dimethyldithiophosphorylacetic acid;

Diphenylsulfides, for example p-chlorobenzyl or p-chlorophenyl sulfide and 2,4,4',5-tetrachloridiphenylsulfide;

Diphenylsulfonates, for example p-chlorophenylbenzenesulfonate;

Methylcarbinols, for example, 4,4-dichloro-1-trichloromethylbenzhydrol;

Quinoxaline compounds, such as methylquinoxaline dithiocarbonate;

Amidines such as N'-(4-chloro-O-tolyl)N,N-dimethylformamidine;

Pyrethroids such as Allethrin;

Biologicals such as *Bacillus thuringiensis* preparations;

Organic tin compounds such as tricyclohexyltin hydroxide;

Synergists such as piperonyl butoxide;

Fungicides such as:

Organic mercury compounds, for example phenylmercuryacetate and methylmercurycyanoguanide;

Organic tin compounds, for example triphenyltin hydroxide and triphenyltin acetate;

Alkylenebisdithiocarbamates, for example, zincethylenebisthiocarbamate and manganoethylenebisthiocarbamate; and furthermore 2,4-dinitro-6-(2-octyl-phenylcrotonate), 1-bis(dimethylamino)phosphoryl-3-phenyl-5-amino-1,2-4-triazole, 6-methylquinoxaline-2,3-dithiocarbonate, 1,4-dithioantraquinone-2,3-dicarbonitrile, N-trichloromethylthiophthalimide, N-trichloromethylthiotetrahydrophthalimide, N-(1,1,2,2-tetrachloroethylthio)-tetrahydrophthalimide, N-dichlorofluoromethylthio-N-phenyl-N'-dimethylsulfonyldiamide and tetrachloroisophthalonitrile.

Compounds according to the present invention were evaluated for their biological activity.

In evaluating the foliar insecticidal activity of the compounds of this invention, the following test procedures were employed.

A test solution containing 600 parts per million (ppm) was made by dissolving the test compound in a solvent (acetone:methanol, 1:1), adding water to give an acetone:methanol:water system of 5:5:90 and then a surfactant. A 1:1 mixture of an alkylarylpolyetheralcohol (sold under the trademark Triton ® X-155) and a modified phthalic glycerol alkyl resin (sold under the trademark Triton ® B-1956) was utilized at the equivalent of 1 ounce per 100 gal. of test solution as a surfactant.

Analogous solutions are made by serially diluting the 600 ppm test solution with water and surfactant to give concentrations of 150, 38, 10, 2.5, 0.6, 0.15, and 0.038 ppm. Not all compounds are tested at each of the several concentrations stated above. Particular concentrations of a particular compound tested are predicated upon responses obtained in a less definite range-finding assay. Test concentrations of a compound are selected as those most likely to differentiate the dose response of a particular compound toward a particular test insect.

Initial evaluations were made on all of the following pests:

| Code Symbol | Common Name | Latin Name |
| --- | --- | --- |
| SAW | Southern Armyworm | *Spodoptera eridania* |
| MBB | Mexican Bean Beetle | *Epilachna varivestis* |
| GPA | Green Peach Aphid | *Myzus persicae* |
| TSM | Two-Spotted Spider Mite | *Tetranychus urticae* |

For the bean beetle and armyworm tests, individual bean (*Phaseolus limensis* var. Woods' Prolific) leaves are placed on moistened pieces of filter paper in Petri dishes. The leaves are then sprayed with the test solution using a rotating turntable and allowed to dry. The dishes are infested with 10 third instar larvae of Southern armyworm or Mexican bean beetle. The dishes are then covered.

The percent mortality for each test species and spray concentration is determined 48 hours after treatment. Mortalities obtained are plotted on logarithmic probability paper (No. 3228, Codex Book Co., Inc., Norwood, Mass.). The estimated concentration eliciting a 50 percent mortality ($LC_{50}$) is established from the best eye-fitted line to the plotted mortality data.

For the mite and aphid tests, a pad of moistened cotton is placed in a Petri dish half. Upon one position of this pad is placed a bean (*Phaseolus limensis*) leaf section (approximately 0.75×0.75 inch). Approximately 50 adult female mites are then brushed onto this leaf section. Upon another portion of the cotton pad is placed an infested broccoli (*Brassica oleracea italica* var. DiCicco) leaf containing about 20 adult and immature aphids. The dish, now containing both targets, is then sprayed with the test solution using a rotating turntable. The open dishes are held for 24 hours at which time the percent mortality is determined for each test species and spray concentration. Derivation of $LC_{50}$ values is as noted for Southern armyworm and Mexican bean beetle.

The rotating turntable consists of a fixed, continuously operating spray nozzle under which targets are rotated at a fixed speed and distance. If the target is a Petri dish (such as for the bean beetle, armyworm, mite or aphid), the distance from the nozzle is 15 inches. The nozzle is located 8 inches from the rotating shaft. The targets on individual platforms revolve around the shaft at 1 revolution per 20 seconds but only a brief portion of this time occurs in the spray path. Targets pass only once under the nozzle and then are removed to drying hoods.

The nozzle used is a ¼ JCO Spraying Systems (Wheaton, Ill.) air atomizing nozzle equipped with a No. 2850 fluid cap and No. 70 air cap. At the 10 psig air pressure used and with liquid siphon feed 0.5 GPH (gallons per hour) are delivered in a round spray pattern with a 21° spray angle. Targets are misted with spray droplets to the point that the droplets coalesce to form a uniform thin film insufficient to drown test organisms.

Systemic activity of the compounds of the present invention was also evaluated employing the following test procedures.

Test solutions are prepared as stated above for foliar insecticidal evaluations. A 10 ml portion of 150 ppm test solution is thoroughly mixed with 200 g of standard greenhouse soil mixture affording 7.5 ppm concentration of test compound in the soil. Approximately 4 week old broccoli (*Brassica oleracea italica* var. DiCicco) or tobacco (*Nicotiana tabacum* var. Greider) seedlings are infested with about 50 aphids per seedling and transplanted into 3-inch pots containing the treated soil and allowed to grow. Similarly, 10 ml of a 5 ppm test solution thoroughly mixed with 200 g of soil affords 0.25 ppm concentration of test compound in the soil; 10 ml of a 20 ppm test solution thoroughly mixed with 200 g of soil affords 1 ppm concentration of test compound in the soil; 10 ml of a 60 ppm test solution thoroughly mixed with 200 g of soil affords 3 ppm concentration of test compound in the soil; 10 ml of an 80 ppm test solution thoroughly mixed with 200 g of soil affords 4 ppm concentration of test compound in the soil; and 10 ml of a 180 ppm test solution thoroughly mixed with 200 g of soil affords 9 ppm concentration of test compound in the soil. The percentage kill is then determined.

All treatments are maintained under existing greenhouse conditions.

The results of the foliar insecticidal evaluations are given in Table II. The selectivity of the compounds of this invention towards aphids is apparent from the results in Table II. Table III sets forth the results of a foliar evaluation comparing a known 1,2,4-triazole outside the scope of the present invention with the compound of Example 2 of the present invention. The results of the systemic insecticidal evaluations of the compounds of the present invention are given in Tables IV and V, along with the results of various known 1,2,4-triazoles outside the scope of the present invention for comparison purposes.

TABLE II

Foliar Insecticidal Evaluations $LC_{50}$ Values[1]

| Example No. | TSM | GPA | MBB | SAW |
|---|---|---|---|---|
| 1 | >600 | 1.2 | 300 | >600 |
| 2 | >600 | 2.4 | 300 | 600 |
| 3 | >600 | 19 | 2.5[a] | >600 |
| 4 | >600 | 5 | 300 | >600 |
| 5 | >600 | 5 | 178 | >600 |
| 6 | >600 | 5 | <150 | >600 |
| 7 | >600 | 1.2 | 300 | >600 |
| 8 | >600 | 1.2 | 192 | >600 |
| 9 | >600 | 5 | 75 | >600 |
| 10 | >600 | 1.2 | >600 | >600 |
| 11 | >600 | 5 | <150 | >600 |
| 12 | >600 | 5 | >600 | >600 |
| 13 | >600 | 41 | >600 | >600 |
| 14 | >600 | 300 | >600 | >600 |
| 15 | >600 | >600 | >600 | >600 |
| 16 | >600 | 19 | 400 | >600 |

[1]Concentration in parts per million (ppm) which kills 50 percent of the stated insect ($LC_{50}$).
[a]48 hour result. After 96 hours some insects that were moribund at 48 hours recovered such that a 96 hour $LC_{50}$ of 45 ppm is probably more descriptive of activity.

For the purposes of comparison, a known 1,2,4-triazole outside the scope of the present invention was foliarly evaluated against a compound of the present invention by the methods described above. The results are presented below in Table III.

TABLE III

Foliar Comparative Evaluation

| Compound or Example No. | Rate (ppm) | % Kill at 24 Hours GPA |
|---|---|---|
| Example 2 of this invention | 2.5 | 50 |
|  | 10 | 100 |
|  | 38 | 100 |
| 1-N,N—dimethylcarbamoyl-3-ethoxycarbonylmethyl-mercapto-5-methyl-1,2,4-triazole (U.S. Pat. No. 3,308,131) | 2.5 | 0 |
|  | 10 | 0 |
|  | 38 | 0 |

TABLE IV

Systemic Insecticidal Evaluations
Green Peach Aphids on Broccoli
(Comparison of Compounds of this Invention With Those of the Prior Art)

| Example No. or 5-position Substituent | Rate of Active Ingredient in soil (ppm) | % Control at 9 Weeks Broccoli |
|---|---|---|
| Example 2 of this invention | 0.25 | 47 |
|  | 1 | 100 |
|  | 4 | 100 |
|  | 7.5 | 100 |
| Prior Art Compounds 5-position substituents |  |  |
| —SCH$_3$[1] | 1 | 0 |
|  | 4 | 22 |
|  | 7.5 | 50 |
| —SCH$_2$CH=CH$_2$[2] | 7.5 | 0 |
| —SCH$_2$SCH$_3$[3] | 7.5 | 0 |
| —SCH$_2$CH$_2$CH$_2$CH$_2$CH$_3$[4] | 7.5 | 25 |
| —SCH$_2$CH$_2$C$_6$H$_5$[4] | 7.5 | 44 |

[1]U.S. Pat. No. 4,054,664
[2]U.S. Pat. No. 4,160,839
[3]U.S. Pat. No. 4,291,043
[4]U.S. Pat. No. 3,308,131

TABLE V

Systemic Biological Evaluations
Green Peach Aphids on Tobacco
(Comparison of Compounds of this Invention
With Those of the Prior Art)

| Example No. or 5-position Substituent | Rate of Active Ingredient in Soil (ppm) | % Control at 21 Days Tobacco |
|---|---|---|
| 1 | 1 | 73 |
|   | 3 | 78 |
|   | 9 | 100 |
| 2 | 1 | 93 |
|   | 3 | 100 |
|   | 9 | 100 |
| 4 | 1 | 93 |
|   | 3 | 90 |
|   | 9 | 100 |
| 5 | 1 | 44 |
|   | 3 | 59 |
|   | 9 | 95 |
| 6 | 1 | 11 |
|   | 3 | 54 |
|   | 9 | 66 |
| 7 | 1 | 52 |
|   | 3 | 59 |
|   | 9 | 78 |
| 8 | 1 | 90 |
|   | 3 | 88 |
|   | 9 | 93 |
| 9 | 1 | 37 |
|   | 3 | 57 |
|   | 9 | 88 |
| Prior Art Compounds | | |
| —SCH$_3$[1] | 1 | 15 |
|   | 3 | 57 |
|   | 9 | 93 |
| —SCH$_2$CH=CH$_2$[2] | 1 | 0 |
|   | 3 | 0 |
|   | 9 | 0 |
| —SCH$_2$SCH$_3$[3] | 1 | 0 |
|   | 3 | 0 |
|   | 9 | 90 |
| —SCH$_2$CH$_2$CH$_2$CH$_2$CH$_3$[4] | 1 | 0 |
|   | 3 | 53 |
|   | 9 | 88 |
| —SCH(CH$_2$CH$_3$)$_2$[4] | 1 | 0 |
|   | 3 | 0 |
|   | 9 | 0 |

[1] U.S. Pat. No. 4,054,664
[2] U.S. Pat. No. 4,160,839
[3] U.S. Pat. No. 4,291,043
[4] U.S. Pat. No. 3,308,131

The results in Tables II, III, IV and V demonstrate compounds of the present invention are unexpectedly superior in their aphicidal activity than similar known compounds.

Certain of the compounds of the present invention have also demonstrated an observable plant growth regulator effect, such as, for example, stunting of plant height, darkening of the hue of foliage, increase in number, size and thickness of leaves, earlier flowering and suckering. The suckering (branching) occurs below the primary leaves and at the point of leaf stem attachments to the main stem. This branching tissue blooms and gives fruit. An increase in root modulation on soybeans has also been observed. It is believed the plant growth regulator effects observed will provide increased yields.

The plant growth regulator effects of certain compounds of the present invention were evaluated both foliarly and systemically.

Test solutions containing 1200 ppm, 600 ppm and 300 ppm were made as stated above for evaluating foliar insecticidal activity. An emulsifiable concentrate formulation containing 4 pounds of active ingredient per gallon was also tested and was prepared as follows. All percentages are by weight unless otherwise indicated.

| | |
|---|---|
| Toxicant (90% active ingredient) | 53.3 |
| Sponto ® 232T (emulsifier) | 5.0 |
| Sponto ® 234T (emulsifier) | 5.0 |
| Tenneco ® T500-100 (solvent) | 36.7 |
| | 100.0 |

All ingredients are mixed together with continuous agitation until a homogenous solution is obtained. Formulated material is added to water so as to give concentrations of toxicant equivalent to those of the above-described test solutions.

Lima bean (*Phaseolus limensis* var. Wood's Prolific) and soybean (*Glycine max.* var. Williams) seedlings (about two weeks old) in 6-inch pots were sprayed to runoff with the test solutions using a DeVilbiss atomizer at 20 psig. When dry, each treatment is maintained under greenhouse conditions. Plants are watered as needed.

For systemic evaluations, the same plant varieties used for foliar plant growth regulator evaluation are used. The soil in which two-week old seedlings in 6-inch pots are planted is drenched with the test solution or equivalent 600 ppm active ingredient concentration of the formulation. The volume of material added to soil results in a 30 ppm (weight by volume) concentration in the soil. Each treatment is maintained under greenhouse conditions as noted above and watered as needed.

For foliar evaluation, observations were made 3 days, 7 days, 14 days and 21 days after application, then held until harvest (about 10 weeks). The plant growth regulator effects were first observed at about one week.

For systemic evaluation, observations were made 7 days, 14 days and 21 days after application. The plant growth regulator effects were first observed at about three weeks.

When used as plant growth regulators, the compounds of the present invention may be applied in any amount which will be sufficient to effect the desired plant response without causing any undesirable or phytotoxic response.

A preferred method of applying a compound of the present invention as a plant growth regulator agent is by foliar application. The compounds of this invention can be used as plant growth regulators either individually or in mixture. For example, they can be used in combination with other plant growth regulators such as auxins, gibberellins, ethylene-releasing agents such as ethephon, pyridones, pyridazinones, cytokinins, maleic hydrazide, succinic acid 2,2-dimethylhydrazide, (2-chloroethyl)trimethylammonium chloride, triiodobenzoic acid, tributyl-2,4-dichlorobenzylphosphonium chloride, polymeric N-vinyl-2-oxazolidinones, tri(dimethylaminoethyl)phosphate and its salts and N-dimethylamino-1,2,3,6-tetrahydrophthalamic acid and its salts and the like.

The compounds of this invention may be applied to the growth medium or to the plants to be treated either by itself or, as is generally done, as a component in a growth regulant composition or formulation which also comprises an agronomically acceptable carrier. By "agronomically acceptable carrier" is meant any substance which can be used to dissolve, disperse or diffuse a compound in the composition without impairing the effectiveness of the compound and which by itself has no significant detrimental effect on the soil, equipment, crops or agronomic environment. Mixtures of the compounds of the invention may also be used in any of these formulations. The compositions of the invention can be either solid or liquid formulations or solutions. These compositions and formulations have previously been described.

Certain of the compounds of the present invention exhibit molluscicidal activity. In evaluating the molluscicidal activity, the following test procedures were employed.

Mature brown garden snails, *Helix aspersa*, were placed into rectangular plastic boxes (32 cm L×25 cm W×15 cm H) containing 5 cm of moistened artificial soil. Ten snails were introduced into each container. Fiberglass screening, held in place with rubber bands, was used as a container cover to confine the snails.

Test compounds were formulated in a wheat bran-based bait at a level of 1% active ingredient. Fifteen grams of loose bait were applied to the soil surface in five equal piles, one in each corner and one in the center.

The snails were offered the test bait for a 5-day period at which time mortality was recorded.

The results of the molluscicidal evaluation are given below in Table VI.

TABLE VI

| | Molluscicidal Evaluation | |
|---|---|---|
| Example No. | Bait Toxicant Concentration | Five Day Mortality |
| 2 | 1.0 | 100% |

It is to be understood that the present specification and examples are set forth by way of illustration and not limitation, and that various modifications and changes may be made without departing from the spirit and scope of the present invention as defined by the appended claims.

We claim:

1. A compound having the formula:

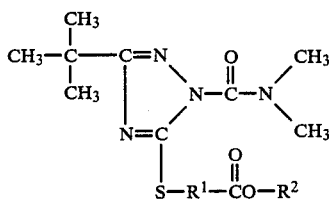

wherein
R$^1$ is an unsubstituted or substituted (C$_1$-C$_{10}$)alkylidene (—(CH$_2$)$_n$—) group having one to four of the same or different substituents selected from CO$_2$R or (C$_1$-C$_6$)alkyl and
R$^2$ is hydrogen or (C$_1$-C$_6$)alkyl;
where R is hydrogen or (C$_1$-C$_6$)alkyl; and agronomically acceptable salts thereof.

2. The compound according to claim 1 wherein
R$^1$ is —CH$_2$—, —CH$_2$CH$_2$—, —CH$_2$CH$_2$CH$_2$— or —CH(CH$_3$)—;
R$^2$ is hydrogen or (C$_1$-C$_4$)alkyl; and agronomically acceptable salts thereof.

3. The compound according to claim 2 wherein
R$^1$ is —CH$_2$—; and
R$^2$ is methyl.

4. The compound according to claim 2 wherein
R$^1$ is —CH$_2$—; and
R$^2$ is ethyl.

5. The compound according to claim 2 wherein
R$^1$ is —CH$_2$—; and
R$^2$ is t-butyl.

6. The compound according to claim 2 wherein
R$^1$ is —CH(CH$_3$)—; and
R$^2$ is ethyl.

7. The compound according to claim 2 wherein
R$^1$ is —CH(CH$_3$)—; and
R$^2$ is methyl.

8. The compound according to claim 2 wherein
R$^1$ is —CH$_2$CH$_2$CH$_2$—; and
R$^2$ is ethyl.

9. The compound according to claim 2 wherein
R$^1$ is —CH$_2$CH$_2$—; and
R$^2$ is methyl.

10. The compound according to claim 2 wherein
R$^1$ is —CH$_2$—; and
R$^2$ is n-propyl.

11. The compound according to claim 2 wherein
R$^1$ is —CH$_2$—; and
R$^2$ is isopropyl.

12. The compound according to claim 2 wherein
R$^1$ is —CH$_2$—; and
R$^2$ is hydrogen.

13. A homopteracidal composition comprising a compound according to claim 1 and an agronomically acceptable carrier.

14. The composition according to claim 13 wherein said compound is present at from about 0.001 to about 75% by weight of the composition.

15. The composition according to claim 13 wherein said carrier comprises particulate material.

16. The composition according to claim 13 wherein said carrier comprises liquid material.

17. The composition according to claim 13 wherein said compound is 1-dimethylcarbamoyl-3-t-butyl-5-(carbomethoxy)methylthio-1H-1,2,4-triazole.

18. The composition according to claim 13 wherein said compound is 1-dimethylcarbamoyl-3-t-butyl-5-(carboethoxy)methylthio-1H-1,2,4-triazole.

19. The composition according to claim 13 wherein said compound is 1-dimethylcarbamoyl-3-t-butyl-5-(carbo-t-butoxy)methylthio-1H-1,2,4-triazole.

20. The composition according to claim 13 wherein said compound is 1-dimethylcarbamoyl-3-t-butyl-5-((1-carboethoxy)eth-1-yl)thio-1H-1,2,4-triazole.

21. The composition according to claim 13 wherein said compound is 1-dimethylcarbamoyl-3-t-butyl-5-((1-carbomethoxy)eth-1-yl)thio-1H-1,2,4-triazole.

22. The composition according to claim 13 wherein said compound is 1-dimethylcarbamoyl-3-t-butyl-5-((3-carboethoxy)prop-1-yl)thio-1H-1,2,4-triazole.

23. The composition according to claim 13 wherein said compound is 1-dimethylcarbamoyl-3-t-butyl-5-((2-carbomethoxy)eth-1-yl)thio-1H-1,2,4-triazole.

24. The composition according to claim 13 wherein said compound is 1-dimethylcarbamoyl-3-t-butyl-5-(carbo-n-propoxy)methylthio-1H-1,2,4-triazole.

25. The composition according to claim 13 wherein said compound is 1-dimethylcarbamoyl-3-t-butyl-5-(carboisopropoxy)methylthio-1H-1,2,4-triazole.

26. The composition according to claim 13 wherein said compound is 1-dimethylcarbamoyl-3-t-butyl-5-(carboxy)methylthio-1H-1,2,4-triazole.

27. A method of controlling insects of the order Homoptera which comprises applying to the insects or to the loci to be freed or protected from attack by insects an insecticidally effective amount of a compound according to claim 1.

28. The method of claim 27 wherein said insects are aphids.

29. The method of claim 27 wherein said compound is applied at from about 10 to about 5000 grams per hectare.

30. The method of claim 29 wherein said compound is applied at from about 50 to about 2500 grams per hectare.

31. The method of claim 27 in which said loci comprises plants or an area where plants are to be grown.

32. The method of claim 31 wherein said compound is applied to allow root absorption and transport.

33. The method of claim 27 wherein the compound is 1-dimethylcarbamoyl-3-t-butyl-5-(carbomethoxy)methylthio-1H-1,2,4-triazole.

34. The method of claim 27 wherein the compound is 1-dimethylcarbamoyl-3-t-butyl-5-(carboethoxy)methylthio-1H-1,2,4-triazole.

35. The method of claim 27 wherein the compound is 1-dimethylcarbamoyl-3-t-butyl-5-(carbo-t-butoxy)-methylthio-1H-1,2,4-triazole.

36. The method of claim 27 wherein the compound is 1-dimethylcarbamoyl-3-t-butyl-5-((1-carboethoxy)eth-1-yl)thio-1H-1,2,4-triazole.

37. The method of claim 27 wherein the compound is 1-dimethylcarbamoyl-3-t-butyl-5-((1-carbomethoxy)eth-1-yl)thio-1H-1,2,4-triazole.

38. The method of claim 27 wherein the compound is 1-dimethylcarbamoyl-3-t-butyl-5-((3-carboethoxy)-prop-1-yl)thio-1H-1,2,4-triazole.

39. The method of claim 27 wherein the compound is 1-dimethylcarbamoyl-3-t-butyl-5-((2-carbomethoxy)eth-1-yl)thio-1H-1,2,4-triazole.

40. The method of claim 27 wherein the compound is 1-dimethylcarbamoyl-3-t-butyl-5-(carbo-n-propoxy)-methylthio-1H-1,2,4-triazole.

41. The method of claim 27 wherein the compound is 1-dimethylcarbamoyl-3-t-butyl-5-(carboisopropoxy)-methylthio-1H-1,2,4-triazole.

42. The method of claim 27 wherein the compound is 1-dimethylcarbamoyl-3-t-butyl-5-(carboxy)methylthio-1H-1,2,4-triazole.

43. The compound according to claim 1 wherein
$R^1$ is an unsubstituted or substituted ($C_1$–$C_4$)alkylidene group having one or two of the same or different substituents selected from $CO_2R$, methyl or ethyl;
$R^2$ is hydrogen or ($C_1$–$C_5$)alkyl; and
R is ($C_1$–$C_4$)alkyl; and agronomically acceptable salts thereof.

44. The compound according to claim 43 wherein
$R^1$ is an unsubstituted or substituted ($C_1$–$C_3$)alkylidene group having one or two of the same or different substituents selected from $CO_2R$ or methyl;
$R^2$ is hydrogen or ($C_1$–$C_4$)alkyl; and
R is ($C_1$–$C_3$)alkyl; and agronomically acceptable salts thereof.

* * * * *